United States Patent
Obias et al.

(10) Patent No.: US 9,782,333 B2
(45) Date of Patent: Oct. 10, 2017

(54) ORAL COMPOSITION FOR XEROSTOMIA

(71) Applicant: Chattem Inc., Chattanooga, TN (US)

(72) Inventors: Honorio Velasco Obias, Ooltewah, TN (US); Shane Christian Smith, Ooltewah, TN (US); Thomas Karl Knopp, Signal Mountain, TN (US); Sarah Elizabeth Torgeson, Chattanooga, TN (US); Ryan Christopher Orr, Chattanooga, TN (US); Sherry Lynn McGraw, Chattanooga, TN (US)

(73) Assignee: CHATTEM INC., Chattanooga, TN (US)

( * ) Notice: Subject to any disclaimer, the term of this patent is extended or adjusted under 35 U.S.C. 154(b) by 0 days.

(21) Appl. No.: 14/601,766

(22) Filed: Jan. 21, 2015

(65) Prior Publication Data
US 2016/0206523 A1   Jul. 21, 2016

(51) Int. Cl.

| | |
|---|---|
| *A61K 8/49* | (2006.01) |
| *A61K 8/25* | (2006.01) |
| *A61K 8/55* | (2006.01) |
| *A61K 8/97* | (2017.01) |
| *A61K 8/21* | (2006.01) |
| *A61K 8/60* | (2006.01) |
| *A61K 8/34* | (2006.01) |
| *A61K 8/42* | (2006.01) |
| *A61Q 11/00* | (2006.01) |
| *A61K 8/81* | (2006.01) |

(52) U.S. Cl.
CPC ........... *A61K 8/34* (2013.01); *A61K 8/347* (2013.01); *A61K 8/42* (2013.01); *A61K 8/8147* (2013.01); *A61Q 11/00* (2013.01); *A61K 2800/5922* (2013.01)

(58) Field of Classification Search
USPC .......................................... 424/48, 58, 725
See application file for complete search history.

(56) References Cited

U.S. PATENT DOCUMENTS

| | | | |
|---|---|---|---|
| 5,035,882 A * | 7/1991 | Hussein et al. | 424/58 |
| 6,159,459 A | 12/2000 | Hunter et al. | |
| 6,780,443 B1 * | 8/2004 | Nakatsu et al. | 424/734 |
| 7,776,923 B2 | 8/2010 | Gatfield et al. | |
| 8,435,542 B2 | 5/2013 | Manley et al. | |
| 2009/0175806 A1 * | 7/2009 | Modak et al. | 424/58 |
| 2009/0220625 A1 * | 9/2009 | Herrmann et al. | 424/756 |
| 2012/0128599 A1 * | 5/2012 | Schaeffer-Korbylo et al. | 424/48 |

FOREIGN PATENT DOCUMENTS

| | | |
|---|---|---|
| EP | 2416766 B1 | 4/2014 |
| WO | WO 2006/013081 | 2/2006 |
| WO | WO 2009/032404 | 3/2009 |
| WO | WO 2011/056759 | 5/2011 |

OTHER PUBLICATIONS

Veryser, L., et al., "N-alkylamides: from plant to brain", Functional Foods in Health & Disease, 4:264-275 (2014).
Bonacucina, G., et al., "Rheological, mucoadhesive and release properties of Carbopol gels in hydrophilic cosolvents" Int'l J.of Pharmaceutics 282:115-130 (2004).
Kotodziejska, J. "Carbopol 974P in the prescription of dental anti-inflammatory hydrogels" Polim. Med. 38(1):27-38 (2008).

* cited by examiner

*Primary Examiner* — Walter Webb
(74) *Attorney, Agent, or Firm* — Hylton-Rodic Law PLLC

(57) ABSTRACT

The present invention discloses an oral composition comprising a combination of salivating agents and gum sensates in an orally acceptable carrier useful in treating and/or alleviating the symptoms associated with xerostomia.
Additional components common in oral compositions may also be used, in order to potentiate the effect. Such components may be chosen among humectants, mucoadhesive polymers, water retention agents, antioxidants, antimicrobials, breath fresheners.

13 Claims, No Drawings

ORAL COMPOSITION FOR XEROSTOMIA

BACKGROUND OF THE INVENTION

Xerostomia, also known as dry mouth, is a condition in which an excessive dryness within the oral cavity takes place, due to insufficient salivary production. Xerostomia is not a disease itself, but is associated with several medical conditions, such as side effects of a variety of medications. Some common problems associated with xerostomia include constant sore throat, burning sensations, difficulty speaking and swallowing and dry nasal passages, all related to the decreased level of fluids in the oral cavity.

The consequences of dry mouth may affect the quality of life, by increasing the risk of caries and periodontal diseases, and also causing bad breath and bad taste to the mouth.

Xerostomia may be alleviated by the consumption of fluids, chewing gums, oral sprays, mouthwashes and throat lozenges. Artificial saliva and proper substitutes are also used in palliative treatments. Examples of artificial salivas include compositions which contain ions that mimic those found in natural saliva, glycerin, as well as carboxymethylcellulose-based preparations to provide the proper level of viscosity.

Therefore, there is an unmet need of oral composition aimed to address this condition.

Several prior art compositions tried to solve the problem, by means of different approaches. WO 2009/032404 discloses oral compositions with a first component having a cation-sensitive mucoadhesive polymer, such as gellan gum and carrageenan, and a second component having an encapsulated cation-releasing compound, such as calcium and sodium salts, both components maintained separate from each other until application to the oral cavity.

WO 2011/056759 discloses compositions for treating xerostomia comprising polyethylene oxide with a molecular weight from 200,000 to 7,000,000, an antibacterial agent, and a sensate, such as a flavor, a sweetener, a coolant, a saliva stimulant or a TRPV1 activator.

U.S. Pat. No. 6,159,459 discloses the use of beta-glucan to coat the surfaces of the oral cavity, thus alleviating the discomfort associated with xerostomia.

WO 2006/013081 discloses the use of a combination of PVP or a derivative thereof with an anionic mudoadhesive polymer, such as a cellulose gum or a saccharide gum.

The present invention has a different approach to alleviating xerostomia. The oral composition herein described a combination of salivating agents and gum sensates in an orally acceptable carrier.

SUMMARY OF THE INVENTION

In one embodiment, the invention discloses an oral composition that comprises:
 a) salivating agents;
 b) gum sensates;
 in an orally acceptable carrier.

Additional components common in oral compositions may also be used, in order to potentiate the effect. Such components may be chosen among humectants, mucoadhesive polymers, water retention agents, antioxidants, antimicrobials, and breath fresheners.

In another embodiment, the invention discloses a method of treating and/or alleviating the symptoms associated with xerostomia by the use of an oral composition that comprises:
 a) salivating agents;
 b) gum sensates;
 in an orally acceptable carrier.

DETAILED DESCRIPTION

The term "oral composition" as used herein means a product that in its ordinary course of usage is retained in the oral cavity for a time sufficient to contact substantially all of the dental surfaces and/or oral tissues for purposes of oral activity. The oral composition of the present invention may be in various forms including toothpaste, dentifrice, rinses, gels, edible films, lozenges, sprays, tooth powders, subgingival gels, or denture products. The oral composition may also be incorporated onto strips or films for direct application or attachment to oral surfaces.

The term "dentifrice" as used herein means paste, gel, powder, tablets, or liquid formulations, unless otherwise specified, that are used to clean the surfaces of the oral cavity.

Oral Composition

The composition of the present invention is an oral composition that comprises:
 a) salivating agents;
 b) gum sensates;
 in an orally acceptable carrier.

Salivating Agents

Suitable salivating agents include those agents capable of long-lasting moisturisation in the oral cavity.

It may act via nerve stimulation (via secondary processes transduced by interaction of trigeminal and parasympathetic nerves) and/or via osmotic pressure.

Suitable salivating agents include, without limitation, trans-pellitorin, spilanthol, sanshool, hydroxy α-sanshool, hydroxy β-sanshool, hydroxy γ-sanshool, sanshool I, sanshool II, sanshoamide, piperine, chavicine, 4-(1-menthoxymethyl)-2-phenyl-1,3-dioxolane, effervescing agents and analogs thereof. Other tingling sensates can be found in U.S. Pat. No. 5,545,424 which is herein incorporated by reference.

The total amount of salivating agent in the composition ranges from 0.001-4.00% w/w.

Gum Sensates

Suitable gum sensates are those compounds that are able to modulate nociceptors perception of pain or inflammatory pain sensation.

Some embodiments may comprise a TRPV1 activator, a transient receptor potential vanilloid receptor 1 activator. These activators may not only off-set bad tastes, but may also reduce dryness perception, by limiting the mouth's ability to perceive dryness.

In one embodiment, the gum sensate is chosen from the group comprising vanillyl butyl ether, zingerone, capsaicin, capsiate, shoagol, gingerol, piperine, bisabolol, 4-t-butyl cyclohexanol, such as Symsitive® or a combination thereof.

The total amount of gum sensates in the composition ranges from 0.001-4.00% w/w.

Orally Acceptable Carrier

The term "orally acceptable carrier" as used herein means a suitable vehicle, which can be used to apply the present compositions to the oral cavity in a safe and effective manner. Such vehicle may include materials such as fluoride ion sources, antibacterial agents, anticalculus agents, buffers, other abrasive materials, peroxide sources, alkali metal bicarbonate salts, thickening materials, humectants, water, surfactants, titanium dioxide, flavor system, sweetening agents, cooling agents, xylitol, coloring agents, and mixtures thereof.

The following is a non-limiting list of actives that may be used in the present invention. The total amount mentioned here should only be considered in cases where said component is indeed present in the formulation.

Fluoride Compound

The present invention may comprise a safe and effective amount of a fluoride compound (e.g. water soluble). Representative fluoride ion sources include: stannous fluoride, sodium fluoride, potassium fluoride, amine fluoride, sodium monofluorophosphate, zinc fluoride, and many others. In one embodiment the composition comprises stannous fluoride or sodium fluoride, as well as mixtures thereof. Fluoride ion may also be considered an antibacterial active, as it has been shown to effectively reduce bacterial activity in the mouth.

The total amount of fluoride compound in the composition ranges from 0.001-4.00% w/w.

Anticalculus/Antitartar Agents

The oral compositions may contain tartar control agents including salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate and phosphonoalkane carboxylic acids. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The oral compositions may also contain an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. The pyrophosphate salt may be present in one of three ways: predominately dissolved, predominately undissolved, or a mixture of dissolved and undissolved pyrophosphate. The preferred composition involves dissolved pyrophosphate with a minimum concentration of 1% free pyrophosphate ions for clear mouthwash and dentifrice applications. Disodium dihydrogen pyrophosphate, tetrasodium pyrophosphate, and tetrapotassium pyrophosphate are the preferred species.

The total amount of pyrophosphate compounds in the composition ranges from 0.1-6.00% w/w. Free pyrophosphate ions may be present in a variety of protonated states depending on a the pH of the composition.

Buffering Agents

The oral compositions may contain a buffering agent. Buffering agents, as used herein, refer to agents that can be used to adjust the pH of the oral compositions to a range of about pH 3.0 to about pH 10.0. The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate.

The total amount of buffering compound in the composition should be sufficient to attain the desired pH. Preferably, it ranges from 0.01-3.00% w/w.

Coloring Agents

Coloring agents may also be added to the present composition. Pigments, pealing agents, filler powders, talc, mica, magnesium carbonate, calcium carbonate, bismuth oxychloride, zinc oxide, and other materials capable of creating a visual change to the oral compositions may also be used. Titanium dioxide may also be added to the present composition. Titanium dioxide is a white powder which adds opacity to the compositions.

The total amount of colorant in the composition ranges from 0.00001-1.00% w/w.

Abrasive Polishing Materials

An abrasive polishing material may also be included in the oral compositions. The abrasive polishing material contemplated for use in the compositions of the present invention can be any material that does not excessively abrade dentin. Typical abrasive polishing materials include silicas, including gels and precipitates; aluminas; phosphates including orthophosphates, polymetaphosphates, and pyrophosphates; and mixtures thereof. Specific examples include hydrated silica, dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde. Mixtures of abrasives may also be used. The most preferred abrasive is hydrated silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels.

Dental abrasives, like the dental polishing agents, also cause a small amount of enamel erosion which is termed "polishing" action. The removal of plaque and calculus prevents caries and periodontal disease. The polishing of teeth removes stains from tooth surfaces, but has not been shown to improve dental health over and above the effects of the removal of plaque and calculus.

The total amount of abrasive polishing material in the composition ranges from 1.0-25.0% w/w.

Mucoadhesive Agents

Additional mucoadhesive agents, such as polymeric thickeners, may be utilized. Suitable mucoadhesive agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Mucoadhesive agents can include polymeric polyether compounds, e.g., polyethylene or polypropylene oxide (M.W. 300 to 7,000,000).

A suitable class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly the carbopols include Carbopol 934, 940, 941, 956, 971P, 974P and mixtures thereof.

The total amount of mucoadhesive agent in the composition ranges from 0.001-16.00% w/w.

Humectant

A humectant can help to keep the oral composition from hardening upon exposure to air and provide a moist feel in the mouth. A humectant or additional solvent may be added to the oral composition. Suitable humectants for the present invention include water, edible polyhydric alcohols such as glycerin, sorbitol, xylitol, butylene glycol, polyethylene glycol, propylene glycol, erythritol, maltitol, isomalt, lactitol, diglycerin, hydrogenated starch hydrolysate (HSH), and combinations thereof. Sorbitol, glycerin, water, and combinations thereof are preferred humectants.

The total amount of humectants in the composition ranges from 10-90% w/w.

Water Retention Agents

Suitable water retention agents are those capable of avoiding the loss of water molecules.

Examples of suitable agents include, without limitations, beta glucan soluble fibers, such as oat beta glucan, trimethyglycine, L-carnosine, and other aminoacids.

The total amount of water retention agents in the composition ranges from 0.001-2.00% w/w.

Surfactants

A surfactant may be added to the oral composition. Surfactants, also commonly referred to as sudsing agents, may aid in the cleaning or foaming of the oral composition. Suitable surfactants are those which are reasonably stable and foam throughout a wide pH range. The surfactant may be anionic, nonionic, amphoteric, zwitterionic, cationic, or mixtures thereof.

Examples of anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Examples of other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics (for example, poloxamers of the form PEO-PPO-PEO), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Typical alkyl dimethyl betaines include decyl betaine or 2-(N-decyl-N,N-dimethylammonio) acetate, coco betaine or 2-(N-coc-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

The total amount of surfactant in the composition ranges from 2.00%-8.00% w/w.

Sensorial Cues

Microbeads may be used in the present formulation for providing sensorial cues. It may contain encapsulated saliva flow stimulants, encapsulated freshening agents and encapsulated cooling agents.

Additional Ingredients

Apart from the ingredients mentioned above, the composition according to the invention may comprise conventional ingredients, such as sweeteners, flavors and soothing botanicals.

Examples

The table below illustrates several toothpaste compositions according to the invention.

TABLE 1

Toothpaste compositions

| Ingredient | Form 2 | Form 3 | Form 4 |
|---|---|---|---|
| Glycerin | 30.0 | 30.0 | 30.0 |
| Sorbitol | 25.0 | 25.0 | 25.0 |
| Hydrated silica (Zeodent 165) | 5.0 | 5.0 | 5.0 |
| Hydrated silica (Zeodent 113) | — | — | — |
| Xanthan gum | 1.0 | 2.0 | 2.0 |
| Carbomer (Carbopol 974P) | 0.20 | 0.40 | 0.20 |
| PEG-14M (Polyox 205) | 0.0050 | 0.0050 | 0.0050 |
| PEG-160M (Polyox 303) | 0.0050 | 0.0050 | 0.0050 |
| Xylitol | 10.0 | 10.0 | 10.0 |
| Titanium Dioxide | — | — | — |
| Water | 20.0170 | 19.4219 | 18.7069 |
| Sodium fluoride | — | — | — |
| Sodium monofluorophosphate | 1.1530 | 1.1530 | 1.1530 |
| Tetrasodium pyrophosphate | 1.0 | 1.0 | 1.0 |
| Sodium benzoate | — | — | — |
| Betaine (trimethylglycine) | 0.010 | 0.010 | 0.010 |
| Sucralose (25% solution) | 1.0 | 1.2 | 1.2 |
| Dipotassium glycyrrhizinate (DPG) | — | 0.005 | 0.010 |
| Cocoamidopropyl betaine | — | — | — |
| Sodium lauryl sarcosinate (Hamposyl L-30) | 4.0 | 4.0 | 4.0 |
| Benzoic acid | 0.30 | 0.30 | 0.30 |
| Spilanthol (Sensingle TAK-112683) | 0.010 | — | — |
| 4-t-butylcyclohexanol (Symsitive 510117) | 0.10 | 0.10 | 0.10 |
| Bisabolol, *Zingiber officinale* (ginger) root extract (Symrelief 100) | 0.010 | 0.010 | 0.010 |

TABLE 1-continued

Toothpaste compositions

| Ingredient | Form 2 | Form 3 | Form 4 |
|---|---|---|---|
| 0.80% Peppermint + 0.10% Eucaliptus oil + 0.05% Trans-pellitorin (Optaflow M) (Symrise Chattem mint blend 417818) | — | — | — |
| Masking Flavor | 0.20 | 0.20 | 0.20 |
| Angelica root | 0.010 | 0.010 | 0.010 |
| Pueraria root | 0.010 | 0.010 | 0.010 |
| Honeysuckle colorant | 0.010 | 0.010 | 0.010 |
|  | 0.000050 | 0.000075 | 0.000075 |
| Oat beta glucan soluble fiber (DentaGlucan) | 0.050 | 0.050 | 0.050 |
| beta-alanyl-L-histidine (L-carnosine) | 0.010 | 0.010 | 0.010 |
| Trans-pellitorin (Optaflow M) | — | 0.100 | 0.010 |
| Eucaliptus oil 100223 | 0.100 | — | — |
| Peppermint flavor 100625 | 0.800 | 1.000 | 1.000 |

TABLE 2

Toothpaste compositions

| Ingredient | Form 6 | Form 7 | Form 8 |
|---|---|---|---|
| Glycerin | 15.0 | 15.0 | 15.0 |
| Sorbitol | 25.0 | 25.0 | 25.0 |
| Hydrated silica (Zeodent 165) | 2.5 | 2.5 | 2.5 |
| Hydrated silica (Zeodent 113) | 15.0 | 15.0 | 15.0 |
| Xanthan gum | 1.0 | 1.0 | 1.0 |
| Carbomer (Carbopol 974P) | 0.400 | 0.250 | 0.400 |
| PEG-14M (Polyox 205) | 0.005 | 0.005 | 0.005 |
| PEG-160M (Polyox 303) | 0.005 | 0.005 | 0.005 |
| Xylitol | 10.00 | 10.00 | 10.00 |
| Titanium Dioxide | 0.50 | 0.50 | 0.50 |
| Water | 21.7070 | 22.0070 | 21.7170 |
| Sodium fluoride | — | — | — |
| Sodium monofluorophosphate | 1.1530 | 1.1530 | 1.1530 |
| Tetrasodium phosphate | 1.0 | 1.0 | 1.0 |
| Sodium benzoate | 0.10 | 0.10 | 0.10 |
| Betaine (BP-20) | 0.010 | 0.010 | 0.010 |
| Sucralose (25% solution) | 1.0 | 1.0 | 1.0 |
| Dipotassium glycyrrhizinate (DPG) | 0.01 | 0.01 | 0.01 |
| Cocoamidopropyl betaine | — | — | — |
| Sodium lauryl sarcosinate (Hamposyl L-30) | 4.0 | 4.0 | 4.0 |
| Benzoic acid | 0.30 | 0.30 | 0.30 |
| Spilanthol (Sensingle TAK-112683) | 0.010 | 0.010 | 0.010 |
| 4-t-butylcyclohexanol (Symsitive 510117) | 0.100 | — | 0.100 |
| Bisabolol, Zingiber officinale (ginger) root extract (Symrelief 100) | 0.010 | — | 0.010 |
| 0.80% Peppermint + 0.10% Eucaliptus oil + 0.05% Trans-pellitorin (Optaflow M) (Symrise Chattem mint blend 417818) | — | — | 0.950 |
| Masking Flavor | 0.20 | 0.20 | 0.20 |
| Angelica root | 0.010 | — | 0.010 |
| Pueraria root | 0.010 | — | 0.010 |
| Honeysuckle colorant | 0.010 | — | 0.010 |
| Oat beta glucan soluble fiber (DentaGlucan) | — | 0.050 | — |
| beta-alanyl-L-histidine (L-carnosine) | 0.010 | 0.010 | — |
| Trans-pellitorin (Optaflow M) | 0.05 | — | — |
| Eucaliptus oil 100223 | — | 0.100 | 0.100 |
| Peppermint flavor 100625 | — | 0.800 | 0.800 |

TABLE 3

Toothpaste compositions

| Ingredient | Form 9 | Form 10 | Form 11 | Form 12 |
|---|---|---|---|---|
| Glycerin | 15.0 | 15.0 | 25.0 | 25.0 |
| Sorbitol | 25.0 | 25.0 | — | — |
| Hydrated silica (Zeodent 165) | 2.5 | 2.5 | 2.5 | 2.5 |
| Hydrated silica (Zeodent 113) | 15.0 | 15.0 | 15.0 | 15.0 |
| Xanthan gum | 1.0 | 1.0 | 1.0 | 1.0 |
| Carbomer (Carbopol 974P) | 0.40 | 0.40 | 0.40 | 0.40 |
| PEG-14M (Polyox 205) | 0.0050 | — | — | — |
| PEG-160M (Polyox 303) | 0.0050 | — | — | — |
| Xylitol | 10.0 | 10.0 | 20.0 | 20.0 |
| Titanium Dioxide | 0.50 | 0.50 | 0.50 | 0.50 |
| Water | 22.6270 | 23.6770 | 28.8870 | 28.8870 |
| Sodium fluoride | 0.2430 | 0.2430 | 0.2430 | 0.2430 |
| Sodium monofluorophosphate | — | — | — | — |
| Tetrasodium phosphate | 1.0 | — | — | — |
| Sodium benzoate | 0.10 | 0.10 | 0.10 | 0.10 |
| Betaine (trimethylglycine) | 0.010 | — | — | — |
| Sucralose (25% solution) | 1.0 | 1.0 | 1.0 | 1.0 |
| Dipotassium glycyrrhizinate (DPG) | 0.010 | 0.010 | 0.010 | 0.010 |
| Cocoamidopropyl betaine | — | — | — | 4.00 |
| Sodium lauryl sarcosinate (Hamposyl L-30) | 4.0 | 4.0 | 4.0 | — |
| Benzoic acid | 0.30 | 0.30 | 0.30 | 0.30 |
| Spilanthol (Sensingle TAK-112683) | 0.010 | 0.010 | 0.010 | 0.010 |
| 4-t-butylcyclohexanol (Symsitive 510117) | 0.10 | 0.10 | 0.10 | 0.10 |
| Bisabolol, Zingiber officinale (ginger) root extract (Symrelief 100) | 0.010 | 0.010 | — | — |
| 0.80% Peppermint + 0.10% Eucaliptus oil + 0.05% Trans-pellitorin (Optaflow M) (Symrise Chattem mint blend 417818) | 0.950 | 0.950 | 0.950 | 0.950 |
| Masking Flavor | 0.20 | 0.20 | — | — |
| Angelica root | 0.010 | — | — | — |
| Pueraria root | 0.010 | — | — | — |
| Honeysuckle colorant | 0.010 | — | — | — |
| Oat beta glucan soluble fiber (DentaGlucan) | — | — | — | — |
| beta-alanyl-L-histidine (L-carnosine) | — | — | — | — |
| Trans-pellitorin (Optaflow M) | — | — | — | — |
| Eucaliptus oil 100223 | — | — | — | — |
| Peppermint flavor 100625 | — | — | — | — |

A survey with xerostomic patients was made comparing 3 formulations according to the invention and 2 marketed compositions (A—Biotene Gentle Mint Gel; B—Biotene PBF Gel).

TABLE 4

Efficacy of formulations according to the invention

|  |  | A | B | Form 2 | Form 3 | Form 4 | Significance |
|---|---|---|---|---|---|---|---|
| Taste | Hedonic | n = 6  3.5 b | 3.6 b | 6.0 a | 6.7 a | 6.8 a | SD |
| Minty Taste | Intensity | n = 6  1.8 b | 1.8 b | 5.7 a | 6.0 a | 5.7 a | SD |

TABLE 4-continued

Efficacy of formulations according to the invention

|  |  |  | A | B | Form 2 | Form 3 | Form 4 | Significance |
|---|---|---|---|---|---|---|---|---|
| Sweet Taste | Intensity | n = 6 | 3.3 | 4.2 | 4.7 | 5.2 | 5.3 | NSD |
| Bitter Taste | Intensity | n = 6 | 2.8 | 2.6 | 3.5 | 2.8 | 4.0 | NSD |
| Texture | Hedonic | n = 6 | 3.2 b | 2.6 b | 5.5 a | 6.5 a | 6.0 a | SD |
| Foaming | Intensity | n = 6 | 2.0 b | 1.8 b | 4.7 a | 5.0 a | 5.2 a | SD |
| Fresh Feeling | Intensity | n = 6 | 2.8 b | 2.6 b | 6.2 a | 6.2 a | 5.5 a | SD |
| Moisturized | Intensity | n = 6 | 2.7 b | 3.0 b | 6.0 a | 6.8 a | 5.8 a | SD |
| Salivation | Intensity | n = 6 | 2.7 b | 1.4 b | 5.0 a | 5.8 a | 5.2 a | SD |

Hedonic: hedonic scale (1 = dislike extremely-9 = like extremely);
Intensity: Intensity scale (1 = low-9 = high);
SD: significant difference at the 95% confidence level.
Like letters following means indicate no significant difference (NSD) between those means. If the letters are different, there is a significant difference between those mean scores.

The results show that for several criteria analyzed, the formulations according to the invention performed better than the prior art's. The results, shown in Table 4, clearly show that the difference of moisturization and salivation imparted by the formulations under analysis was statistically significant when compared with the prior art formulations.

The invention claimed is:

1. An oral composition for treating and/or alleviating the symptoms associated with xerostomia comprising:
   a) trans-pellitorin and one or more salivating agents selected from the group consisting of spilanthol, sanshool, hydroxy α-sanshool, hydroxy β-sanshool, hydroxy γ-sanshool, sanshool I, sanshool II, sanshoamide, chavicine, and 4-(1-menthoxymethyl)-2-phenyl-1,3-dioxolane, and combinations thereof;
   b) 4-t-butyl cyclohexanol and one or more gum sensates selected from the group consisting of vanillyl butyl ether, zingerone, capsiate, and bisabolol, and combinations thereof;
in an orally acceptable carrier;
wherein said composition comprises a carbomer, and optionally a polymeric polyether compound.

2. The oral composition according to claim 1, wherein the composition is selected from the group comprising toothpaste, dentifrice, rinses, gels, edible films, lozenges, sprays, tooth powders, subgingival gel and/or denture product.

3. The oral composition according to claim 1, wherein the total amount of salivating agent in the composition ranges from 0.001-4.00% w/w.

4. The oral composition according to claim 1, wherein the total amount of gum sensate in the composition ranges from 0.001-4.00% w/w.

5. The oral composition according to claim 1, wherein the orally acceptable carrier comprises one or more of the following ingredients:
   a) fluoride compound;
   b) anticalculus/antitartar agents;
   c) buffering agents;
   d) coloring agents;
   e) abrasive polishing materials;
   f) mucoadhesive agents;
   g) humectant;
   h) water retention agents;
   i) surfactants;
   j) sensorial cues; and/or
   k) combinations of two or more of the ingredients (a)-(j) above.

6. The oral composition of claim 1, said composition comprising:
   4-t-butyl cyclohexanol, trans-pellitorin, and spilanthol, and bisabolol; and a carbomer.

7. The oral composition according to claim 6, wherein said composition further comprises glycerin, sorbitol, xylitol, butylene glycol, polyethylene glycol, propylene glycol, erythritol, maltitol, isomalt, lactitol, diglycerin, hydrogenated starch hydrolysate (HSH), and combinations thereof.

8. The oral composition according to claim 7, wherein said composition further comprises one or more buffering agents selected from the group consisting of monosodium phosphate, trisodium phosphate, sodium benzoate, benzoic acid, sodium hydroxide, potassium hydroxide, alkali metal carbonate salts, sodium carbonate, imidazole, and pyrophosphate salts.

9. The oral composition according to claim 7, wherein said composition comprises:

| |
|---|
| Glycerin |
| Sorbitol |
| Xylitol |
| Benzoic acid |
| 4-t-butylcyclohexanol |
| Bisabolol, *Zingiber officinale* (ginger) root extract |
| Trans-pellitorin |
| Spilanthol |
| Carbomer. |

10. The oral composition according to claim 6, said mucoadhesive agent comprises one or more carbomers and/or one or more polymeric polyether compounds.

11. The oral composition according to claim 1, wherein the total amount of said carbomer in the composition ranges from 0.001-16.00% w/w.

12. The oral composition according to claim 11, wherein said polymeric polyether compound is selected from the group consisting of polyethylene and polypropylene oxide (M.W. 300 to 7,000,000).

13. The oral composition according to claim 1, wherein the total amount of said polymeric polyether compound in the composition ranges from 0.001-16.00% w/w.

* * * * *